United States Patent [19]

Box et al.

[11] Patent Number: 4,846,186

[45] Date of Patent: Jul. 11, 1989

[54] FLEXIBLE GUIDEWIRE

[75] Inventors: John W. Box, Miami, Fla.; James V. Donadio, Natick, Mass.

[73] Assignee: Cordis Corporation, Miami, Fla.

[21] Appl. No.: 143,008

[22] Filed: Jan. 12, 1988

[51] Int. Cl.$^4$ .............................................. A61B 6/00
[52] U.S. Cl. .................................... 128/657; 128/772; 604/164; 604/280
[58] Field of Search .................... 128/657, 772; 604/9, 604/164, 170, 280, 282

[56]  References Cited

U.S. PATENT DOCUMENTS

| | | | |
|---|---|---|---|
| 4,619,274 | 10/1986 | Morrison | 128/772 |
| 4,721,117 | 1/1988 | Mar et al. | 604/170 |
| 4,763,647 | 8/1988 | Gambale | 128/657 |

Primary Examiner—Max Hindenburg
Assistant Examiner—Randy Citrin
Attorney, Agent, or Firm—Watts, Hoffmann, Fisher & Heinke

[57]  ABSTRACT

A guidewire suited for inserting both diagnostic and therapeutic catheters. The guidewire has an initial uniform diameter segment that is coated with Telfon along a majority of its length. This core station tapers along a uniform portion to a second constant diameter segment surrounded by a flexible spring tip. The core again tapers in a region where the flexible spring separates from the core. The core is then flattened to increase flexibility within the flexible spring and the flattened core and spring are brazed together at a extreme distal tip portion to form a hemispherical distal guidewire tip.

4 Claims, 2 Drawing Sheets

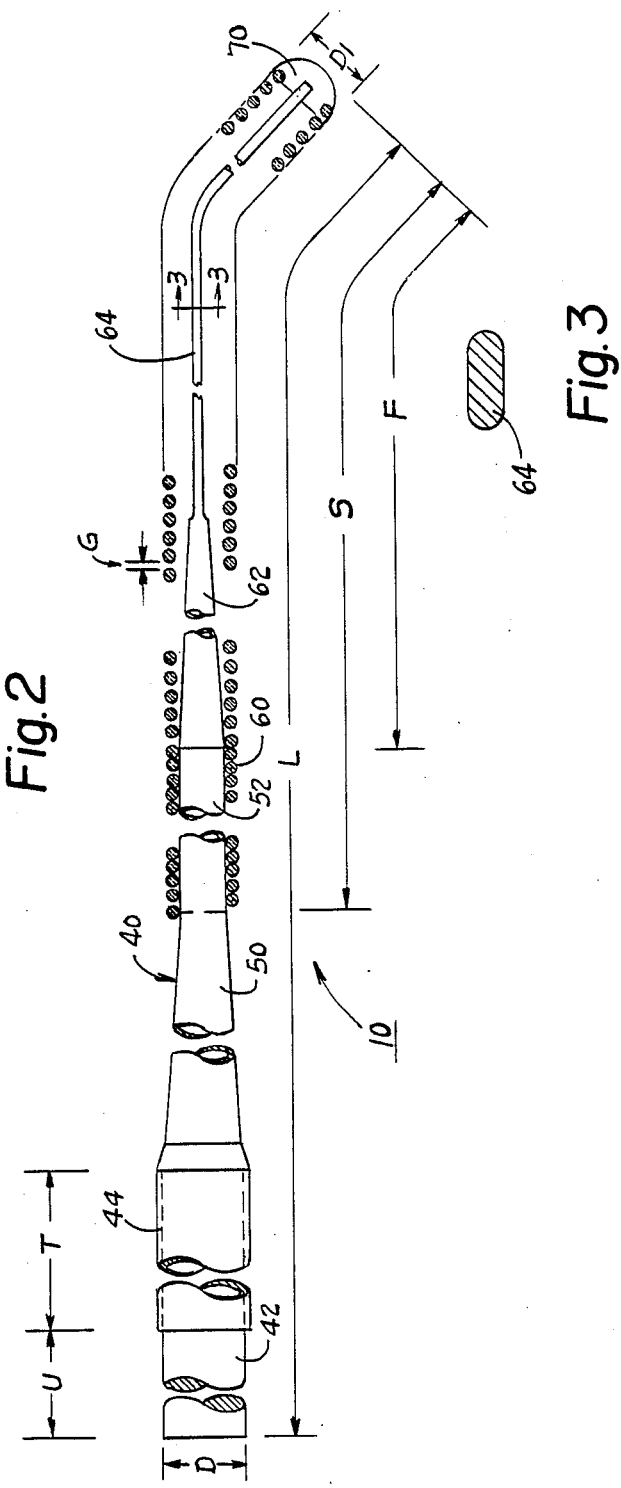

FLEXIBLE GUIDEWIRE

TECHNICAL FIELD

The present invention relates to a flexible elongated guidewire used to position a catheter within a patient.

BACKGROUND ART

Percutaneous Coronary Angioplasty is a therapeutic medical procedure used to increase blood flow through the coronary artery and can often be used as an alternative to coronary by-pass surgery. An elongated catheter having a deflated balloon at its distal end is guided through a patient's cardiovascular system to the coronary artery of the heart. The balloon is inflated to compress deposits that have accumulated along the inner walls of the coronary artery to widen the artery lumen and increase blood flow.

One prior art technique for positioning the balloon catheter uses an elongated guidewire that is inserted into the patient and routed through the cardiovascular system as guidewire progress is viewed on an x-ray imaging screen.

The path the guidewire follows as it is inserted is tortuous. The distal tip is flexible to avoid damaging inner walls of the blood vessels that the guidewire tip contacts along the tortuous path. The distal tip is often pre-bent to a desired configuration so that the guidewire can be inserted into the branching blood vessels along the path. When the tip is pre-bent the physician must be able to orient the tip so it can be pushed into these branching blood vessels.

Representative prior art patents that disclose flexible, elongated guidewires are U.S. Pat. Nos. 4,545,390 to Leary, 4,538,622 to Samson et al. and 3,906,938 to Fleischhacker. The Leary '390 patent discloses a narrow flexible guidewire having a distal portion that tapers and includes a flexible coiled spring at its distal end.

DISCLOSURE OF THE INVENTION

The present invention relates to an elongated flexible guidewire designed for insertion into blood vessels to aid in positioning a catheter within a subject.

In accordance with the invention, an elongated flexible guidewire is constructed from a flexible wire core having a first diameter that extends a major portion of the guidewire from a proximal end to a distal region of the guidewire. At this distal region, the cord tapers uniformly along a first tapered portion to a second lesser diameter portion that is shorter than the first diameter portion. The core wire then again tapers along a second tapered portion in a uniform manner to a final flattened distal portion of the wire core. A flexible coiled wire spring is attached to the core along the length of the lesser diameter portion and separates from the core wire as the core wire tapers along the second tapered portion. Along the lesser diameter portion of the core adjacent coils of the spring are touching. Along the region of the spring spaced from the core adjacent coils are spaced to enhance the flexibility of the guidewire. At the extreme distal tip of the guidewire, the coiled wire spring is again attached to the flattened distal portion of the core wire to form a distal guidewire tip.

This guidewire construction results in a flexible distal guidewire portion which can be pre-bent into a desired orientation and easily oriented by the physician inserting the guidewire. The extreme distal portion of the flattened core is preferably connected to the extreme distal end of the coiled wire by a braze material which forms a rounded convex hemispherical tip which can come in contact with the inner wall of a blood vessel without damaging that blood vessel.

From the above it is appreciated that one object of the invention is a flexible guidewire having a center core wire that tapers in stages at a distal portion of the core and terminates in a flattened end portion that is surrounded by a flexible spring attached to the flattened distal end portion by brazing. This construction produces good flexibility resulting in more easily maneuvering of the guidewire. This and other objects, advantages and features of the invention will become better understood from a detailed description of the invention which is described in conjunction with the accompanying drawings.

BRIEF DESCRIPTION OF THE DRAWINGS

FIG. 2 is an elevation segmented view of a flexible guidewire constructed in accordance with the invention; and FIG. 3 is an enlarged sectioned view as seen from the plane defined by the lines 3—3 in FIG. 2.

BEST MODE FOR CARRYING OUT THE INVENTION

Figure 1:
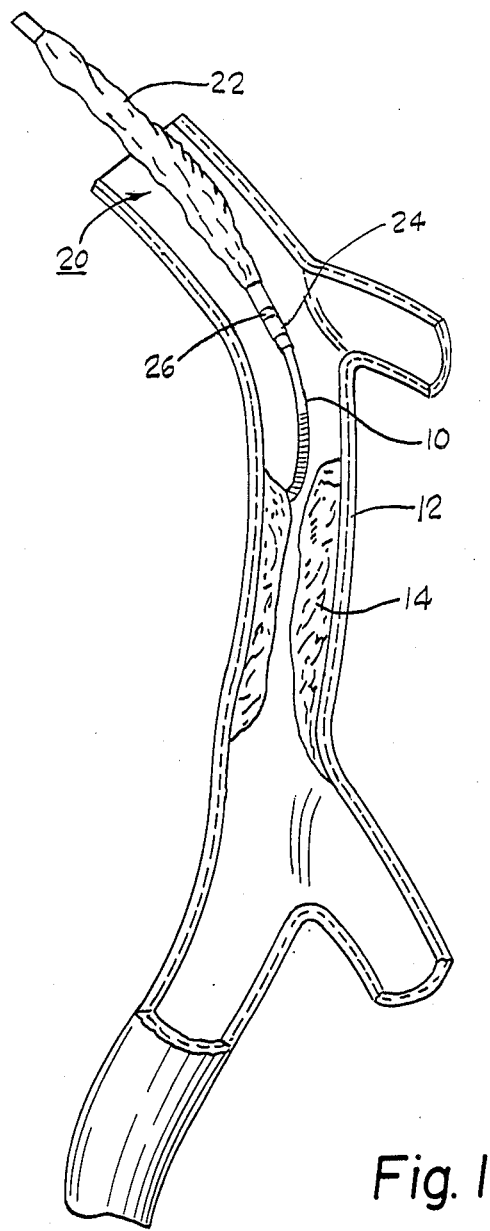
FIG. 1 is a diagrammatic view showing a blood vessel that has been occluded with deposits along an inner wall and shows the positioning of a flexible guidewire within the blood vessel.

Turning now to the drawings, FIG. 1 illustrates a distal portion of a flexible, small diameter guidewire 10 that can be guided through a patient cardiovascular system. A distal end of the guidewire is approaching a region in a blood vessel 12 having occlusions 14 which have restricted blood flow through the blood vessel 12. The guidewire 10 is long enough to be routed from a patient entry point through the patient to the obstructed blood vessel region. In a preferred embodiment the guidewire is 175 cm. long (approximately 69 inches). As the guidewire 10 is inserted along the tortious path to the obstructed blood vessel region, an attending physician conducting the procedure monitors progress of the guidewire 10 on a viewing screen.

The FIG. 1 depiction illustrates use of a guidewire for routing a balloon catheter 20 to the vicinity of the obstructions 14. The balloon catheter 20 includes a first passageway or lumen from a proximal location outside the patient to a distally located balloon 22 that is used to inflate the balloon. A distal tip portion 24 of the catheter 20 includes a marker band 26 to aid the attending physician in monitoring balloon catheter progress as it is positioned within the patient. A second, center passageway or lumen in the catheter 20 has a diameter sufficient to accommodate the guidewire 10 so that once the guidewire is properly positioned the catheter 20 can be slid over the guidewire.

The distal tip portion of the guidewire 10 is flexible and can be bent to a predetermined configuration to facilitate routing the guidewire 10 along the cardiovascular system to the blood vessel 12. The prebent tip can be re-oriented by the physician. Torques applied to the proximal end of the guidewire are transmitted along the length of the guidewire and reorient the distal tip to point in a desired direction.

In use, a distal end of the guidewire 10 is routed through a narrow passageway 14a in the obstruction 14 and the balloon catheter 20 slipped over the guidewire until the balloon 22 bridges the region 14 of obstructions within the blood vessel 12. The balloon 22 is then pressurized from a pressure source outside the patient and as the balloon outer surface contacts the obstruction 14, inner walls of the obstruction are compressed and a wider lumen or passageway created in the blood vessel 12.

Although the FIG. 1 depiction has been used to illustrate one use of the guidewire, it is appreciated that a guidewire constructed in accordance with the invention has utility with angiographic catheters or any application requiring the routing of a tubular device within a patient.

Turning now to FIG. 2, the guidewire 10 is seen to include a center stainless steel wire core 40 having a first uniform diameter portion 42 extending well over half the length "L" of the guidewire. To improve the depiction of details of the distal portion of the guidewire 10, this uniform diameter elongated portion 42 has been sectioned and a major portion of its length deleted in FIG. 2.

The total length of the uniform diameter portion 42 is approximately 148 cm. of the total guidewire length of 175 cm. A proximal segment have a length "U" of the core portion 42 is exposed and the remaining length "T" is covered with a thin Teflon coating 44. The exposed segment "U" can be more easily grasped by the attending physician and also allows a clamping device to be used to rotate the guidewire's proximal end.

The Teflon (Registered Trademark) is applied to the core 40 to a thickness of approximately 0.00065 inch by a hot dipping process. At the region of the distal portion of the Teflon coating 44, the core 40 tapers along a portion 50 in a uniform manner to a second reduced diameter portion 52. The reduced diameter portion 52 is bounded by a coiled wire spring 60.

The wire spring 60 separates from the core 40 where the core begins to taper in a uniform manner along a portion 62. At the region where the spring 60 separates from the core 40, the spring is less tightly coiled to define gaps or spaces "G" of approximately 0.001 inch between adjacent coils. An extreme distal portion 64 of the core 40 is flattened and surrounded by the less tightly coiled portion of the spring 60. As seen in FIG. 2, this distal portion of the guidewire 10 can be pre-bent to a particular configuration by the attending physician to facilitate insertion of the guidewire within the subject.

At the extreme distal tip portion of the guidewire 10, a braze material 70 attaches the distal portion of the spring 60 to the flattened portion 64 of the core. A preferred braze material is a gold alloy that defines a hemispherical bead which covers at least 4 coils and is polished so it does not damage the inner lining of the blood vessels as the tip comes in contact with those linings.

Table I below provides representative dimensions for a preferred guidewire construction and tolerances for those dimensions.

TABLE I

| Dimension (FIG. 2) | (Inches) Nominal | Tolerance |
|---|---|---|
| L | 68.90 | ± .39 |
| D | .0130 | ± .0003 |

TABLE I-continued

| Dimension (FIG. 2) | (Inches) Nominal | Tolerance |
|---|---|---|
| D1 | .0140 | + .0003 / − .0005 |
| U | 2.76 | ± .79 |
| T | 55.51 | ± 1.18 |
| S | 9.84 | + .39 / − .20 |
| F | 1.20 | + .00 / − .20 |

The preferred spring 60 is a platinum/tungsten wire alloy having a percent by weight of 92% platinum and 8% tungsten. The platinum/tungsten wire diameter is approximately 0.002 inches and as noted above, the spring is closely packed so that along the core portion 52 adjacent coils of the spring 60 touch each other. The coils are less tightly packed to define gaps or spaces along the tapered 62 and flattened portions 64 of the core 40. The spring is soldered to the core 40 along two 0.15 inch segments (approximately) of the reduced diameter portion 52 using Utectic Brand No. 157 Silver Base, Cadmium Free, Low Temperature, Surgical Grade Solder. The core 40 is constructed from a uniform diameter stainless steel wire which is centerless ground along the tapered portion 50 to the reduced diameter portion 52 and again ground along the tapered portion 62 to a uniform diameter. The flattened portion 64 is formed by stamping a uniform diameter core portion having an initial diameter of 0.003 inch which when flattened by a die, results in 0.002 inch thick by 0.0045 inch wide flattened portion that "bulges" outward on two sides (FIG. 3).

The guidewire 10 depicted in FIG. 2 is particularly suited for insertion into small diameter blood vessels and can be used, for example, for positioning a balloon in a bridging relationship within the coronary artery.

The dimensions shown in Table I are for a preferred embodiment in the invention for use in small diameter blood vessels. These dimensions are representative of this use and are not intended to limit the invention, but rather define a small diameter guidewire whose characteristics are particularly advantageous. It is the intent, however, that the invention include all modifications and/or alterations from the disclosed dimensions and design falling within the spirit or scope of the appended claims.

We claim:

1. An elongated flexible guidewire for positioning within a patient comprising:
    (a) a flexible wire core having a first diameter portion extending from a proximal end to a distal region of the guidewire and that tapers uniformly along a first tapered portion of said wire core to a second lesser diameter portion shorter than said first diameter portion and that again tapers uniformly along a second tapered portion to a flattened distal portion of said wire core;
    (b) a flexible coiled wire spring that surrounds the wire core and is attached to said core along the length of the second lesser diameter portion of the flexible wire core and that separates from the core wire at a proximal portion of the second tapered portion, extends along the second tapered and flattened distal portions, and is attached to the flattened distal portion of said wire core at a distal end of the guidewire; and (c) a plastic coating covering all but an extreme proximal portion of the first diameter portion of said wire core.

2. The guidewire of claim 1 where the coiled spring is attached to said flattened distal portion of said wire core with a brazing material which forms a rounded distal tip of the guidewire.

3. The guidewire of claim 1 where a portion of the coiled wire spring attached to the second lesser diameter portion of the core is closely packed with adjacent coils touching and a portion of the coiled wire spring that overlies the second tapered and flattened distal portions is wound with gaps between adjacent coils.

4. The guidewire of claim 1 where the coiled wire spring has a relatively uniform diameter from the region attached to the lesser diameter core wire to the portion attached to the distal end of the flattened distal portion.

* * * * *